(12) United States Patent
Cigaina

(10) Patent No.: US 6,321,124 B1
(45) Date of Patent: *Nov. 20, 2001

(54) IMPLANT DEVICE FOR ELECTROSTIMULATION AND/OR MONITORING OF ENDO-ABDOMINAL CAVITY TISSUE

(75) Inventor: Valerio Cigaina, Villorba (IT)

(73) Assignee: Transneuronix, Inc., Mt. Arlington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,324

(22) PCT Filed: May 21, 1998

(86) PCT No.: PCT/US98/10402

§ 371 Date: Jan. 26, 2000

§ 102(e) Date: Jan. 26, 2000

(87) PCT Pub. No.: WO98/53878

PCT Pub. Date: Dec. 3, 1998

(30) Foreign Application Priority Data

May 28, 1997 (IT) .............................................. MI97A1246

(51) Int. Cl.[7] .................................................... A61N 1/05
(52) U.S. Cl. ............................................ 607/133; 600/377
(58) Field of Search ..................................... 607/116, 126, 607/128, 130, 132, 133; 600/372, 373, 375, 377, 381

(56) References Cited

U.S. PATENT DOCUMENTS

| | | |
|---|---|---|
| 2,865,376 | 12/1958 | Pellier et al. . |
| 3,760,812 | 9/1973 | Timm et al. . |
| 4,444,207 | 4/1984 | Robicsek . |
| 4,475,560 | 10/1984 | Tarjan et al. . |
| 4,524,771 | 6/1985 | McGregor et al. . |
| 4,541,440 | * 9/1985 | Parsonnet ............................ 607/132 |
| 4,901,722 | 2/1990 | Noguchi . |
| 5,059,207 | 10/1991 | Shah . |
| 5,100,431 | 3/1992 | Buster et al. . |
| 5,423,872 | 6/1995 | Cigaina . |
| 5,423,876 | 6/1995 | Camps et al. . |
| 5,433,728 | 7/1995 | Kim . |
| 5,450,739 | 9/1995 | Bogart et al. . |
| 5,489,294 | 2/1996 | McVenes et al. . |
| 5,716,392 | 2/1998 | Bourgeois et al. . |

FOREIGN PATENT DOCUMENTS

| | | |
|---|---|---|
| 44 02 058 | 1/1994 | (DE) . |
| WO 97/41921 | 11/1997 | (WO) . |

* cited by examiner

Primary Examiner—George R. Evanisko
(74) Attorney, Agent, or Firm—Fitch, Even, Tabin & Flannery

(57) ABSTRACT

An implant device specifically for electrostimulation and/or electrical monitoring of endo-abdominal tissue or viscera is provided. The implant device has an elongated body equipped with devices to secure it to the tissue to be treated and two or more electric poles that are electrically connected to an electric connection terminal for connection to a power source to penetrate the tissue to be treated, and quick-release connecting devices to separate the penetration device from the elongated body.

15 Claims, 3 Drawing Sheets

IMPLANT DEVICE FOR ELECTROSTIMULATION AND/OR MONITORING OF ENDO-ABDOMINAL CAVITY TISSUE

FIELD OF THE INVENTION

This invention provides an implant device specifically for electrostimulation and/or electrical monitoring of endo-abdominal tissue or viscera. The present implant device has an elongated body equipped with devices to secure it to the tissue or viscera to be treated and two or more electric poles that are electrically connected to an electric connection terminal for connection to a power source, means to penetrate the tissue or viscera to be treated and quick-release connecting devices to separate the penetration device from the elongated body.

BACKGROUND OF THE INVENTION

It is well known that more than 70% of illnesses affecting the digestive tract are of a functional nature. Today such illnesses are treated predominantly using pharmacological means. Since drugs generally have side effects, particularly when the drugs cure the symptom and not the underlying problem or dsyfunction, they must often be administered temporally. Indeed, if the side effects are sufficiently serious, the drug may have to be discontinued before full benefit to the patient is realized; in many cases the underlying illness remains.

The important role played by electrophysiology in controlling gastrointestinal activity has become increasingly apparent in recent years. Thus, the possibility exits of correcting dysfunction by means of electrostimulation applied at the specific frequency, sites, and modalities and with regard to the self-regulating electromotor physiology of the gastrointestinal tube. It has recently been shown, for example, that changes occur in the motility and electromotor conduct of the gastric tract in eating disorders (e.g., obesity, thinness, bulimia, anorexia). Disturbances in electromotor activity in diabetic gastroparesis, reflux in the upper digestive tract, and numerous other gastro-enterological functional pathologies have also been observed.

Stimulation of the intrinsic nervous system of the stomach is likely to have two major consequences or effects: (1) the correction and direct control of the electromotor activity of the intestines and (2) increased production of specific substances (i.e., gastroenteric neuromediators) by the intrinsic nervous system through the myenteric plexus. Curing of functional illnesses involving the digestive system and more broadly involving disorders in any way connected to the digestive system is, therefore, closely linked to the progress of research in the field of electrophysiology.

An indispensable condition for modifying the electrical activity of the digestive systems's intestinal tract and the related neurohormonal incretions is the use of an implant system to generate electrical impulses (electrical stimuli) and electric tubes (electrocatheters) to connect them to the tissue or viscera to be stimulated. These treatment methods involve a surgical technique to implant the electrocatheter in the abdomen which is known as micro-invasive surgery or video-laparoscopic surgery. Current electrocatheters to stimulate electrically and/or monitor endo-abdominal viscera normally have metal microbarbs which are angled in such a way as to permit application of the end of the catheter and to prevent it from being dislodged. However, this type of catheter is often very complicated to make and consequently is very costly.

Moreover, current electrocatheters are generally very difficult to handle and use. More particularly, surgeons generally find them very difficult to insert because of the many arduous operations required to be performed during the laparoscopic procedure. In such procedures, the patient is first given a general anesthetic, after which his or her abdomen is inflated with $CO_2$ or another inert inflammable gas so as to transform the abdominal cavity from a virtual to a real cavity. Rigid tubes with air-tight membranes (i.e., "trocars") are then inserted into the abdominal cavity filled with $CO_2$ so that a video camera and other surgical instruments can be introduced into the abdomen. The operation then proceeds by viewing the video images transmitted by the camera. Normally four or more trocars are used. Generally the first trocar provides access to the abdomen by the video camera in order to monitor the surgical procedure. A service clamp is normally inserted in the second trocar to move or retain the hepatic edge that normally covers the small gastric curve or other viscus depending on the type of operation to be performed. A third trocar provides access for a maneuvering clamp. The fourth trocar is used for the introduction of the electrocatheter to be implanted in the patient. The structure of the electrocatheter plays an important part in facilitating the specific operation for whichever of the patient's viscera the surgeon aims to stimulate.

SUMMARY OF THE INVENTION

An improved implant device for electrostimulation and/or electrical monitoring of the endo-abdominal viscera is provided. The improved implant device of the present invention is simple to handle and use, thereby simplifying the surgical procedure required to implant the device. This implant device can be easily inserted and anchored in the viscera to be stimulated without using any type of suture or requiring any maneuvers that might be difficult and risky for the other viscera or for the integrity of the electrocatheter itself. This improved implant device is especially adapted for electrostimulation and/or electrical monitoring of the tissue or viscera of the mammalian body (especially the human body), especially tissue and internal organs the endo-abdominal cavity. Examples of such tissue and internal organs include, but are not limited to, the stomach, intestines, spleen, bladder, muscles, and the like.

One object of the invention is to provide an implant device specifically for electrostimulation and/or electrical monitoring of the endo-abdominal visceral tract that has significant flexibility of use since it is capable of having multiple poles and of being adapted to any surgical requirement without substantially modifying its structure. Another object of the invention is to provide an implant device specifically for electrostimulation and/or electrical monitoring of the endo-abdominal viscera that the surgeon is able to locate easily in order to determine the orientation of its two ends.

Still another object of the invention is to provide an implant device which, once it is anchored in the viscera, is capable of reducing to a minimum its excessive length inside the abdomen. Another object of the invention is to provide an implant device that effectively protects the electrical connection terminal that connects to a power source so as to be able to perform this operation in a dry arena, thereby permitting the entire procedure, including anesthesia, to be carried out in an extremely short time.

A further object of the invention is to provide an implant device specifically for electrostimulation or electrical monitoring of tissue to be treated within the endo-abdominal cavity, said implant device comprising (1) an elongated body having a distal end and a proximal end, (2) a penetration mechanism at the distal end to penetrate the tissue to be treated, (3) a quick release connecting mechanism adjacent to the penetration mechanism, (4) a first and second sets of flexible tines adjacent and proximal to the quick release connecting mechanism to secure the implant device to the tissue to be treated wherein the first and second sets of tines are spaced apart along the elongated body a distance sufficient to span the tissue, such that the first set of tines are located between the quick release connecting mechanism and the second set of tines, (5) at least two electric poles located between the two sets of flexible tines, and (6) an electrical connection terminal at the proximal end for connection to a power source wherein the two or more electric poles are electrically connected to electrical connection terminal, and wherein the quick release connecting mechanism is effective to separate the penetration device from the elongated body once the implant device is properly positioned in the endo-abdominal cavity.

These and other features and advantages of the present invention will become apparent to those skilled in the art upon a reading of the following detailed description when taken in conjunction with the drawings wherein there is shown and described preferred embodiments of the invention.

DETAILED DESCRIPTION OF THE PREFERRED EMBODIMENTS

Figure 1:
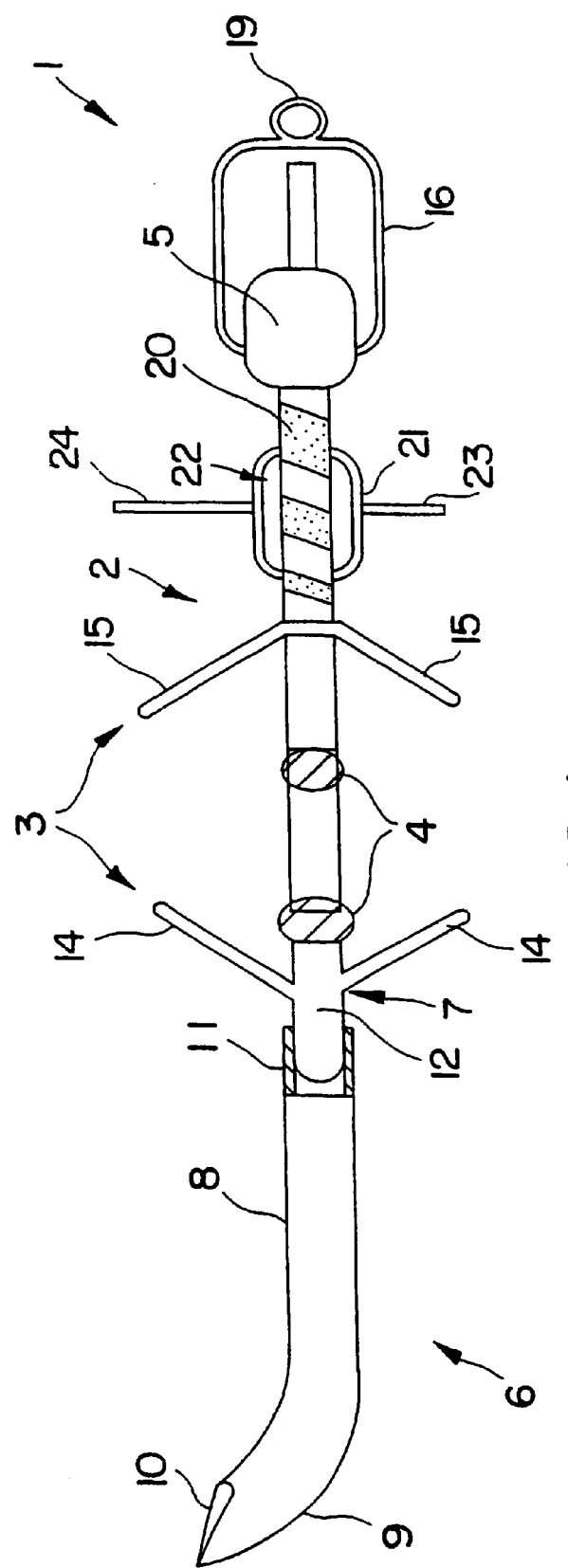
FIG. 1 is a schematic side view of one embodiment of the implant device according to this invention.
Figure 2:
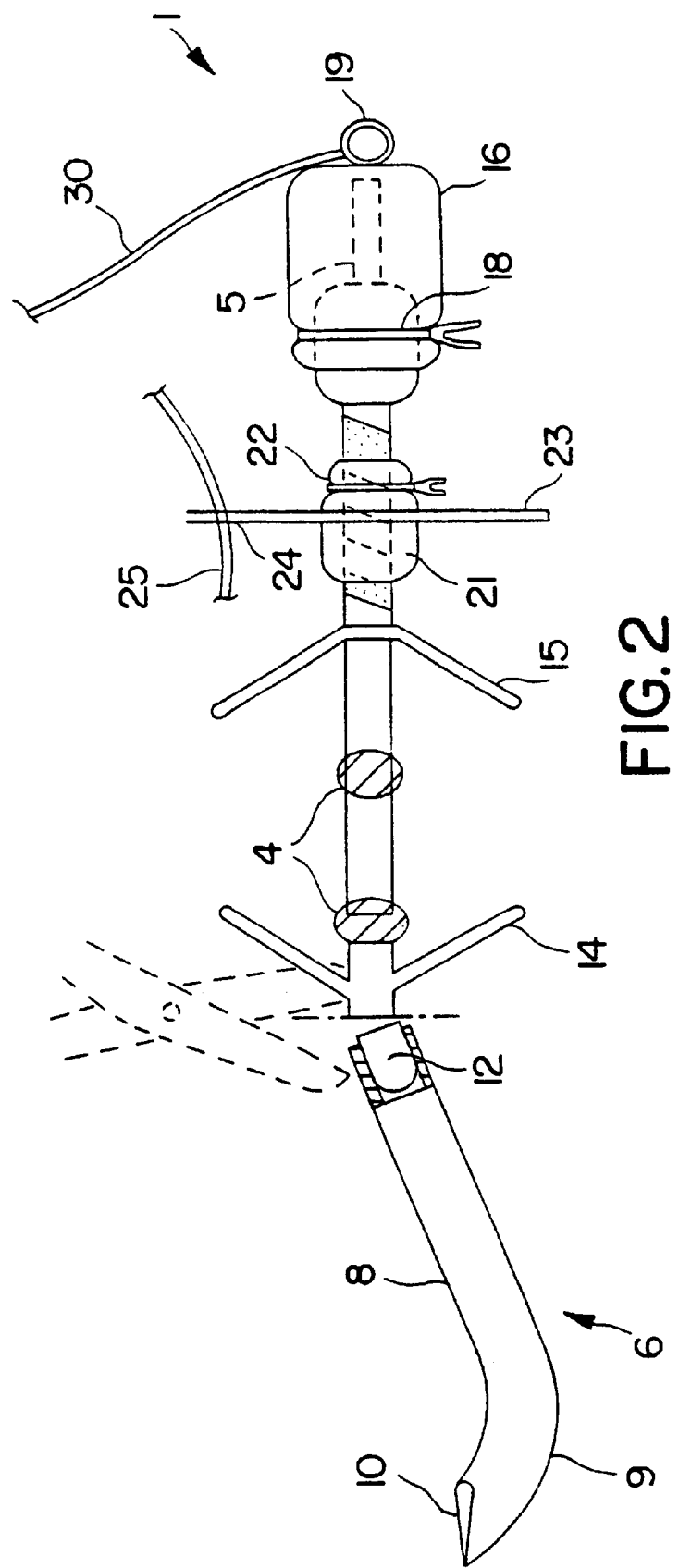
FIG. 2 illustrates how, once the implant device of FIG. 1 has ben inserted during the video-laparoscopic operation, the surgeon can easily remove or detach the visceral wall penetrating mechanism that forms part of the implant device according to this invention.

The present invention provides an implant device specifically for electrostimulation and/or electrical monitoring of the endo-abdominal visceral tract. The implant device has an elongated body equipped with devices to secure it to the intestinal wall and two or more electric poles that are electrically connected to an electrical connection terminal for connection to a power source, characterized by the fact that it includes means to penetrate the intestinal wall and a quick release connecting mechanism to separate said penetration device from the elongated body. One embodiment of the present invention is illustrated in FIGS. 1 and 2. The implant device specifically for electrostimulation and/or electrical monitoring of the endo-abdominal viscera is identified overall by reference number 1, and includes an elongated body 2 of the electrocatheter equipped with securing mechanisms 3 (consisting of tines or wings 14 and 15) to secure it to the visceral wall (not shown), and two or more electric poles 4 which are electrically connected to an electrical connection terminal pin 5 that is capable of connecting the electrocatheter to a power source (not shown). The power source may be, for example, an electric pulsator with an operating frequency of a preset number of pulses per minute.

More specifically, and advantageously, the implant device includes penetration mechanism 6 capable of penetrating the intestinal wall and mechanism 7 for connection and quick-release of penetration mechanism 6 to the elongated body 2 of the electrocatheter. In particular, penetration mechanism 6 includes a solid tunneling device or stylet 8 with a smooth, noncutting curved section 9 on the end of which is cutting part 10. Located opposite end 10 is cavity 11 through which the attachment to the elongated body 2 is made. The connection and quick-release mechanism 7 includes a connecting element 12, one end of which is connected to the end of elongated body 2, and the other end of which is connected to the inside of cavity 11 on stylet 8.

The outer insulating cover on elongated body 2 and connecting element 12 are preferably formed from silicone (preferably medical grade) or other bio-compatible materials having similar stress characteristics. The length of the connecting element 12 is adjusted to permit angling and flexibility without harming the electrical component located within the elongated body. In addition, the connecting element 12 preferably is radiopaque. Advantageously, during video-laparoscopic surgery, in order to separate the stylet 8 from the elongated body 2 of the electrocatheter, it is sufficient to cut it with scissors as shown in FIG. 2 in order to be able to remove the stylet from the abdominal cavity.

Furthermore, as can easily be seen from FIGS. 1 and 2, connecting element 12 also has securing parts 3 and in particular first projections or tines 14 which spread apart and are elastically pliable. Preferably, the securing parts 3 and tines 14 are also made of silicone, but not radiopaque. Opposite the plurality of first tines 14, the elongated body 2 is equipped with a plurality of second tines 15, which spread apart in the opposite directions from the first tines and are designed to define the deepest point of penetration of the elongated body into the visceral wall. Generally, both the first and second tines are each at least two in number; preferably each set of tines are three to five in number. Preferably, the first tines 14 have a diameter of about 1 mm and a length of about 3 mm and should penetrate the entire thickness of the intestinal wall or other tissue to be stimulated before exiting on the opposite side. Preferably, the second set of tines are the same approximate size and shape as the first set of tines. As those skilled in the art will realize, both the first and second set of tines may be of different numbers, sizes, and shapes so long as they serve their intended purpose of "locking" the implant to the tissue or viscera to be simulated and/or monitored. The tines are flexible and are preferably formed from silicone (preferably medical grade) or other bio-compatible materials in order to minimize damage or stress to the tissue as the implant device is positioned and, after completion of treatment, removed. Generally the first tines are located about 3–5 mm in front of the first pole 4 of the electrocatheter (the first pole 4 is that pole located nearer the stylet 8). The first pole of the electrocatheter is obviously the beginning of its active electrical conduction with the second pole (also located between the two sets of tines) completing the active electrical connection with the tissue to be stimulated.

In operation, the second tines 15 do not penetrate the thickness of the intestinal wall or other tissue to be stimulated. Rather, they work with the first pair to prevent the electrocatheter from being dislodged after insertion. In effect, the two sets of tines 14 and 15 allow the electrocatheter to be "locked" in place relative to the tissue to be stimulated without the need for any suturing to anchor the electrocatheter, which could damage it. The distance between the first and second pair of tines may be vary as needed, and will depend upon the desired distance between the cathode and the anode (i.e., the first and second poles 4 located between the two sets of tines). Of course, the desired distance between the two poles will be related to the thickness of the tissue intended to be stimulated. The distance between the cathode and the anode can also vary depending upon whether the electrical simulator is used only for stimulation or for electrical monitoring and/or whether an electrocatheter with several poles is to be used. Preferably, the linear part of stylet 8 has a length that is at least equal to the distance between the first and second sets of tines 14 and 15.

The implant device may also include a cover or cap 16 that consists, for instance, of a removable and insulating sheath which has, in addition, sealing element 18. The sheath includes a small covering, also of silicone, which guarantees both the impermeability of connecting terminal 5 for the entire time it is in the abdomen during insertion, and during its recovery for electrical connection. For this reason the sheath includes the sealing element consisting of binding 18 which keeps it watertight, prevents any contact between the biological fluids and electric terminal 5, and prevents the sheath from breaking off by force of the traction to which it is subjected when the electrical connecting terminal is extracted from the abdomen. The sheath is, moreover, equipped with a means to recover the electrocatheter after implanting, which consists of ring 19 which can be attached to thread 30 of a predetermined length. The unattached end of thread 30 remains outside the abdominal cavity and thereby permits recovery of the electric terminal end of the electrocatheter.

If desired, the elongated body may have a series of graphic representations 20, each one of which is different from the other, which can be used to indicate the orientation and location of the electrocatheter during the implant procedure. The purpose of the graphic representations 20 is to indicate to the surgeon the location of the two ends of the electrocatheter during the insertion operation. For example, the graphic representations could consist of black zebra stripes that increase in size as they moves toward electric terminal 5. Of course, other graphic representations could be used so long as they allow the orientation and location of the electrocatheter to be determined visually (through the video camera) during the implantation procedure.

In addition, the elongated body shown in FIGS. 1 and 2 has a sliding cylindrical cursor 21 equipped with a seat 22 which permits it to be stopped at a desired position on the elongated body. The cursor has a discoidal extension 23 with one or more small holes 24 through which thread 25 may be inserted, which permits the electrocatheter to be attached to a membrane outside the abdominal cavity. After the electrocatheter is anchored to the viscera (i.e., the tissue to be stimulated and/or monitored), the surgeon cam move the small cylinder to the desired position on the electrocatheter and attach it to the outside of the abdominal cavity so as to reduce to a minimum the excessive length of the electrocatheter inside the abdomen itself In operation, once the patient has been given a general anesthesia and the appropriate trocars have been inserted, it is possible to maneuver from outside all the instruments that are used by means of a monitor that transmits the images from the video camera. At this point, the surgeon should see to it that sheath 16 is tightly secured by binding 18 to electrical terminal 5. Then the surgeon proceeds to connect thread 30 to ring 19 attached to sheath 16. After the electrocatheter is placed in the abdominal cavity, the surgeon keeps thread 30, which is anchored to said ring and must be of sufficient length, outside the abdomen. By means of the live images from the camera it is easy to identify the back end of the electrocatheter thanks to the zebra stripes 20 on it, and thus, stylet 8 which is secured by a needle holder or clamp is introduced into the thickness of the small gastric curve, taking care not to enter the gastric cavity. For this purpose, a gastroscopy may be performed during the tunneling operation.

When stylet 8 has completed its journey, it is gently pushed so as to cause the first pair of tines 14 to exit the tunnel created by stylet. The second pair of tines 15 stops outside the tunnel created by the stylet. In this position, the tissue to be stimulated is located between the two pairs of tines 14 and 15. Moreover, the electrocatheter is effectively "locked" in place by the two pairs of tines 14 and 15. Positioned between the two tines, and therefore inside the transmuscular tunnel, are two or more electrical poles 4 to stimulate the gastric wall.

Once the electrocatheter is properly position, the stylet 8 is then again secured with forceps, and quick release connecting element 12 is cut easily and simply with endoscopic scissors as shown in FIG. 2. Preferably, the quick release connecting element 12 is cut as close as possible to the stylet. The stylet is then removed from the abdominal cavity of the patient. Using thread 30 attached to ring 19 on sheath 16 the electric terminal may be extracted from the abdomen for connecting to an appropriate power source or an electric stimulator, for instance, such as a pacemaker or electric recorder.

Once the electric terminal is outside the abdomen, small loop 18 is removed and sheath 16 is removed from electric terminal 5 in order to expose the electric terminal. The operation is thus performed in a dry arena, after surgical gloves have been changed. Electric terminal 5 is then connected to a pacemaker or a recorder, and the proper functioning of the system and the integrity of the electrocatheter are checked using the appropriate instrument. After gently pulling the electrocatheter toward the outside so as to reduce to a minimum length its presence in the abdomen, cursor 21 is slid towards the abdominal wall and is then secured to the electrocatheter using, for example, a nylon thread. The electrocatheter is then anchored via extension 23, by means of thread 25, to the abdominal wall, preferably to the muscular fascia, by a nylon suture. In this manner, the electrocatheter is secured in two positions: (1) around the tissue to be stimulated by tines 14 and 15 and (2) to the abdominal wall via extension 23.

Figure 3:
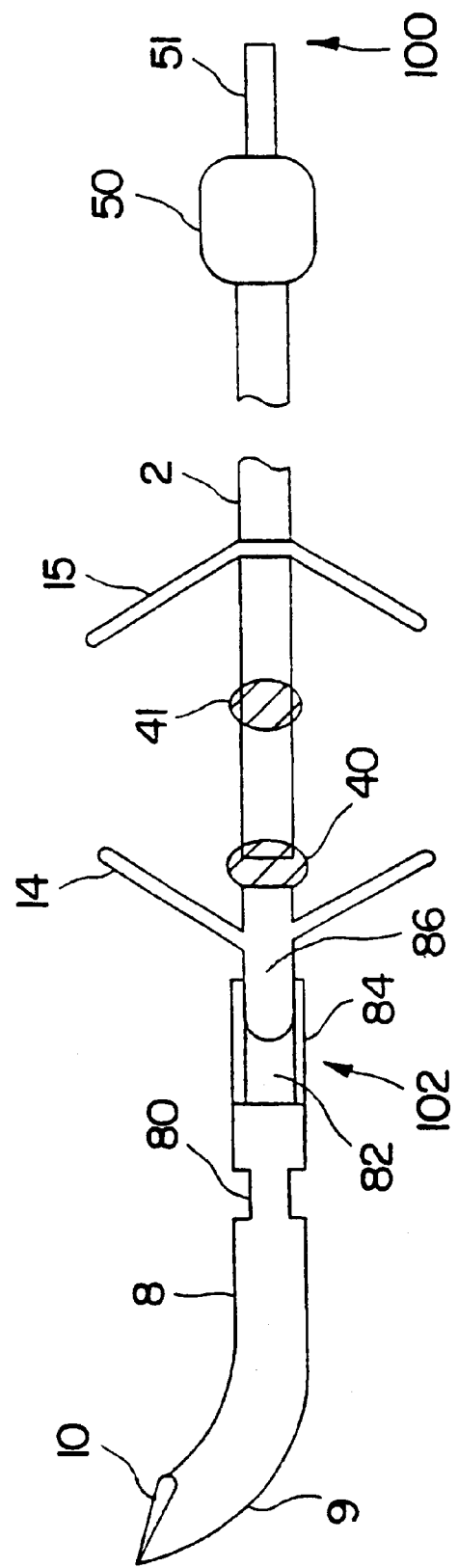
FIG. 3 is a schematic side view of a simplified embodiment of the implant device according to this invention.

A simplified embodiment of the present electrocatheter is shown in FIG. 3 In this embodiment, the stylet 8 is attached to the elongated body 2 at distal end 102. The stylet 8 in this embodiment is attached to the elongated body 2 using a flexible tube 84 (preferably medical-grade silicone similar to the insulating cover of the elongated body 2) that fits over the end 86 of elongated body 2 and the hub 82 of stylet 8. The connection may be strengthen, if desired, using medical-grade adhesive and/or a thin wire joining the stylet 8 and the elongated body 2. Of course, if such a wire is used to strengthen the connection, it should be non-conducting or electrically isolated from the electrical circuit used for stimulation. The elongated body 2 has two opposite set of tines or wings 14 and 15 with the appropriate poles 40 and 41 located there between. The elongated body 2 terminates in electrical terminal 5 having electrical poles 50 and 51 at proximal end 100. In operation, the electrocatheter is placed and positioned in the same manner as described above for the embodiment shown in FIGS. 1 and 2 except that the electrical terminal 5 remains outside the body cavity. Thus, once the electrocatheter has been correctly positioned within the body cavity, the electrical terminal 5 can be attached to the appropriate power source. Thus, the simplified electrocatheter shown in FIG. 3 does not require the movable cursor 21 or the sheath 16 to protect the electrical terminal 5 since the electrical terminal 5 remains outside the body cavity during the implantation procedure. Preferably the stylet 8 has one or more flattened portions 80 to help the surgeon grasp, manipulate, and guide the implant device to the proper position using forceps or other surgical instruments.

In operation, the electrocatheter shown in FIG. 3 is placed using essentially the same surgical procedure as described above. Once in place, the two poles 50 and 51 of electrical terminal 5 are attached to a power source. One pole 50 of the electrical terminal 5 is electrically connected to one pole 40 and the other pole 51 of the electrical terminal 5 is electrically connected to the other pole 41 through the elongated body. The electrical circuit is completed via the tissue to be stimulated and/or monitored. Thus, as those skilled in the art will understand, the overall electrical circuit within the implant device runs from one pole 50 of the electrical terminal 5 along a first electrical path through the elongated body 2 to electric pole 40, through the tissue to be stimulated to the other electric pole 41, and then from the other electric pole 41 through a second and separate electric path through the elongated body 2 to the other pole 51 in the electrical terminal 5. As those skilled in the art will also realize, the materials of construction and the methods of making the electrical circuit for the implant devices of this invention, including the poles 40, 41, 50, and 51 as well as the internal electrical connections, are well known in the art.

It has been proven in practice that the implant device according to the invention is particularly useful as stated above. The invention so described may be subject to numerous modifications and variations, all of which fall within the scope of the inventive concept; furthermore, all the details may be replaced by technically equivalent elements. In practice, the materials used, as well as the dimensions, may be varied according to need and the state of the art. Moreover, although this implant device has been described in the context of use within the endo-abdominal cavity, it can, of course, be used in other portions of the body with appropriate modifications.

What is claimed is:

1. An implantable device specifically for electrostimulation or electrical monitoring of tissue to be treated within the endo-abdominal cavity, said implant device comprising (1) an elongated body having a distal end and a proximal end, (2) a penetration mechanism at the distal end of the elongated body adapted to penetrate the tissue to be treated, (3) a quick release connecting mechanism on the elongated body and adjacent to the penetration mechanism, (4) a first and second sets of flexible tines on the elongated body and adjacent and proximal to the quick release connecting mechanism adapted to secure the implant device to the tissue to be treated wherein the first and second sets of tines are spaced apart along the elongated body a distance sufficient to span the tissue such that the first set of tines are located between the quick release connecting mechanism and the second set of tines, (5) at least two electric poles on the elongated body and located between the two sets of flexible tines, and (6) an electrical connection terminal at the proximal end of the elongated body for connection to a power source wherein the two or more electric poles are electrically connected to the electrical connection terminal, wherein the quick release connecting mechanism is effective to separate the penetration device from the elongated body once the implantable device is properly positioned in the endo-abdominal cavity.

2. A device according to claim 1 further comprising a cover to protect the electrical connection terminal and means to recover the electrical connection terminal of the electrocatheter once the electrostimulation or the electrical monitoring of tissue to be treated has been completed.

3. A device according to claim 1, wherein the penetration mechanism includes a stylet with one smooth curved non-cutting section with a cutting point and a cavity on an opposite end for attachment to the distal end of the elongated body.

4. A device according to claim 3, wherein the quick-release connecting mechanism includes a connecting element, one end of which is connected to the distal end of the elongated body and the other end of which is lodged in the cavity on the stylet.

5. A device according to claim 4, wherein the first set of tines are angled towards the proximal end of the elongated body such that they can pass easily through a tunnel in the tissue to be treated formed by the penetration mechanism and the second set of tines are angled towards the distal end of the elongated body such they resist passage through the tunnel.

6. A device according to claim 4, wherein the elongated body, except the penetration mechanism and the at least two electric poles, which is to be inserted into the endo-abdominal cavity and is to be in direct contact with tissue therein, are formed from medical-grade silicone.

7. A device according to claim 6, wherein the stylet has a flattened portion to allow the stylet to be easily grasped and maneuvered with surgical instruments.

8. A device according to claim 7, wherein the elongated body has a series of graphic representations, each of which is different from the next, which can be used by a surgeon to determine orientation and position of the implantable device in the endo-abdominal cavity during implantation.

9. A device according to claim 4, wherein the stylet has a flattened portion to allow the stylet to be easily grasped and maneuvered with surgical instruments.

10. A device according to claim 3, wherein the stylet has a flattened portion to allow the stylet to be easily grasped and maneuvered with surgical instruments.

11. A device according to claim 1, wherein the first set of tines are angled towards the proximal end of the elongated body such that they can pass easily through a tunnel in the tissue to be treated formed by the penetration mechanism and the second set of tines are angled towards the distal end of the elongated body such they resist passage through the tunnel.

12. A device according to claim 1, wherein the elongated body, except the penetration mechanism and the at least two electric poles, which is to be inserted into the endo-abdominal cavity and is to be in direct contact with tissue therein, are formed from medical-grade silicone.

13. A device according to claim 1, wherein the elongated body has a series of graphic representations, each of which is different from the next, which can be used by a surgeon to determine orientation and position of the implantable device in the endoabdominal cavity during implantation.

14. A device according to claim 1, further comprising a cursor that can slide along the elongated body, wherein the cursor has a seat to lock the cursor at a desired position along the elongated body and wherein the cursor has a discoidal extension with one or more small holes adapted for a thread to be inserted in order to anchor the device with the endo-abdominal cavity.

15. An implantable device for electrostimulation and electrical monitoring of tissue to be treated within a cavity of the human body, said implant device comprising (1) an elongated body having a distal end and a proximal end, (2) a penetration mechanism at the distal end of the elongated body adapted to penetrate the tissue to be treated, (3) a quick release connecting mechanism on the elongated body and adjacent to the penetration mechanism, (4) a first and second sets of flexible tines on the elongated body and adjacent and proximal to the quick release connecting mechanism adapted to secure the implant device to the tissue to be treated wherein the first and second sets of tines are spaced apart along the elongated body a distance sufficient to span the tissue such that the first set of tines are located between the quick release connecting mechanism and the second set of tines, (5) at least two electric poles on the elongated body and located between the two sets of flexible tines, and (6) an electrical connection terminal at the proximal end of the elongated body for connection to a power source wherein the two or more electric poles are electrically connected to the electrical connection terminal, and wherein the quick release connecting mechanism is effective to separate the penetration device from the elongated body once the implantable device is properly positioned in the cavity.

* * * * *